United States Patent [19]

Gazave et al.

[11] 4,015,017

[45] Mar. 29, 1977

[54] CERTAIN BIPHENYL DERIVATIVES USED TO TREAT DISORDERS CAUSED BY INCREASED CAPILLARY PERMEABILITY

[75] Inventors: Jean-Maurice Gazave, Paris; Alain Rancurel, Chartres; Georges Grenier, Epernon, all of France

[73] Assignee: Laboratoires Pharmascience, Courbevoie, France

[22] Filed: Jan. 14, 1975

[21] Appl. No.: 541,022

[30] Foreign Application Priority Data

Jan. 15, 1974 France .............................. 74.01228

[52] U.S. Cl. .............................. 424/331; 424/304; 424/335; 424/346
[51] Int. Cl.$^2$ ........................................ A61K 31/12
[58] Field of Search ........... 424/331, 346; 260/590, 260/591

[56] References Cited

UNITED STATES PATENTS

| 3,068,151 | 12/1962 | Haefele | 424/71 |
| 3,850,988 | 11/1974 | Ruby | 260/591 |
| 3,862,982 | 1/1975 | Welstead | 260/591 X |

OTHER PUBLICATIONS

Chemical Abstracts 57: 11486a (1962).

*Primary Examiner*—Leonard Schenkman
*Attorney, Agent, or Firm*—Alan H. Levine

[57] ABSTRACT

Pharmaceutical compositions the essential active ingredient of which is a biphenyl derivative, at least one of the phenyl nuclei of which has two adjacent hydroxyl groups, the two phenyl nuclei being separated by a carbon chain having one or two carbon atoms and in general, a double bend between two chain carbon atoms or between a chain carbon atom and a substituent thereof. The compositions are useful for the treatment of disorders of the blood micro-circulation.

2 Claims, No Drawings

CERTAIN BIPHENYL DERIVATIVES USED TO TREAT DISORDERS CAUSED BY INCREASED CAPILLARY PERMEABILITY

The present invention relates to pharmaceutical preparations comprising diphenyl derivatives, these preparations being particularly useful for the treatment of disorders in the capillary circulatory system.

The present invention provides a pharmaceutical preparation which comprises, as active ingredient a compound of the general formula I

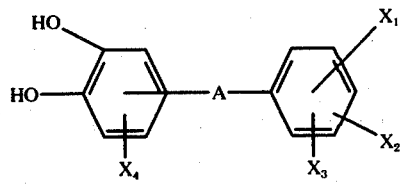

wherein
$X_1$, $X_2$, $X_3$ and $X_4$, which may be the same or different, each represents a hydrogen atom or a hydroxyl group, and A represents the group

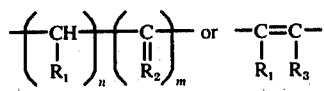

is which
 n represents 0 or 1 and $(m + n)$ equals 1 or 2,
 $R_1$ represents a hydrogen atom or a cyano group,
 $R_2$ represents an oxygen or sulphur atom or a cyclohexylidene, benzomethylide or benzo-1-cyano-1-methylidene group, and
 $R_3$ represents a hydrogen atom or a phenyl group, or an ester or ether thereof, in admixture or conjunction with a pharmaceutically suitable carrier.

The preparations of the invention preferably comprise a compound of the general formula Ia: a compound of the general formula

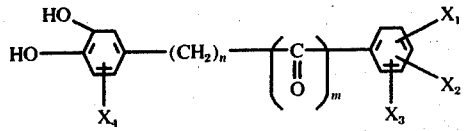

wherein $X_1$, $X_2$, $X_3$, $X_4$, n and m are as defined above, or an ester or ether thereof.

The following are examples of compounds of formula I and Ia which may be used in the pharmaceutical preparations of the invention:
 3,3',4,4'-tetrahydroxybenzophenone,
 3,4-dihydroxybenzophenone,
 3,3',4,4',5'-pentahydroxybenzophenone,
 2,3,4-trihydroxybenzophenone,
 2,3,3',4,4',5'-hexahydroxybenzophenone,
 3,3',4,4'-tetrahydroxybenzil,
 β-(3,4-dihydroxyphenyl)-3,4-dihydroxyacetophenone,
 2,3,3',4,4'-pentahydroxybenzophenone,
 di-(3,4-dihydroxyphenyl)-methane,
 2,3,3',4'-tetrahydroxybenzophenone,
 2,3',4,4'-tetrahydroxybenzophenone,
 2,3',4,4',5'-pentahydroxybenzophenone,
 2,3',4,4',5'-pentahydroxybenzophenone,
 2,3',4,4',5,5'-hexahydroxybenzophenone,
 β-(3,4-dihydroxyphenyl)-2,3,4-trihydroxyacetophenone.

A preparation of the invention may be in a form suitable for oral, rectal, parenteral or topical administration.

The pharmaceutical preparations according to the present invention may comprise one or more of the compounds of formula I, and may also comprise one or more other active compounds, for example, compounds showing vitamin P activity. Convenient forms for oral administration are tablets, granules, hard or soft capsules, dragees, ampoules to be taken orally, suspensions, emulsions, syrups, and elixirs and dispersable powders. The liquid formulations preferably contain a third solvent.

The oral preparations are preferably in unit dosage form, and advantageously comprise from 100 to 500 mg of the active substance per unit dose.

The following is an example of a formulation suitable for oral administration:

| | |
|---|---|
| 2,3,3',4,4',5'-hexahydroxybenzophenone | 100 mg |
| corn maize starch | 100 mg |
| Amijel | 6 mg |
| Lactose | 82 mg |
| Aerosil 200 | 3 mg |
| Magnesium stearate | 3 mg |
| Talc | 6 mg |
| | 300 mg |

The components are mixed in suitable proportions, then granulated by means of steam, compressed and dried in a ventilated drying cupboard to obtain the specified dosage unit.

The carriers which may be used in the preparations of the invention are for example, inert diluents, for example, lactose and calcium carbonates; binding agents, for example, starch and gelatine; granulation agents, for example, maize starch; and lubricating agents, for example, magnesium stearate and talcum. In order to prolong the action of the dosage units, they may be coated with a coating.

The preparations for parenteral administration in particular for intravenously administration, may be in the form of sterile preparations, for example, solutions, or emulsions containing suspension agents, dispersion agents or humidifiers.

The following is an example of a formula for an injectable preparation:

| | |
|---|---|
| 2,3,3',4,4',5'-hexahydroxybenzophenone | 10 mg |
| P E G 300 | 90 mg |
| water | 15 mg |
| | 115 mg or 0.1cc |

Topical formulations, for example, creams and lotions preferably comprise from 2 to 10% of the active ingredient.

Rectal preparations, for example, suppositories, preferably comprise from 50 to 500 mg of the active ingredient.

Particularly important carriers for parenteral, topical and rectal preparations are polyethylene glycols.

The present invention also provides a process for treating disorders of the microcirculation of the blood, notably complaints involving an increase of capillary permeability and complaints involving a decrease in the capillary resistance, for example, retinopathy, purpura, capillarity, oedema of vascular origin, microthrombosis, acrocyanosis, and Raynaud's syndrome, wherein to a patient suffering from a disorder of the microcirculation, there is administered with a therapeutically effective quantity of one or more compounds of the formula I or Ia.

The dose of the compound to be administered is preferably from 1 to 30 mg/kg daily. When administered intravenously, the dose is preferably from 2 to 10 mg/kg daily, and oral dosages are preferably from 10 to 30 mg/kg daily. If necessary these dosages can be increased.

The invention further provides a pack which comprises a compound of the formula I or an ester or ether thereof, together with instructions, the instructions requiring the administration of the compound to a patient to treat disorders of the micro-circulation. The doses to be administered are preferably those indicated above, and the compound is advantageously administered as a pharmaceutical preparation of the invention.

Some of the above described compounds are already known, in particular in the dyeing industry, notably those having two hydroxyl functions adjacent to a ketonic group. Such compounds are mordant dyes, for example, gallobenzophenone, which is known as "alizarin yellow A".

This explains why the processes of preparing the medicaments according to the present invention are so numerous and are in general well known. Thus an aromatic polyhydroxyl ketone of formula I may be prepared by reacting an aromatic carboxylic acid having hydroxyl groups on the phenyl nucleus in the presence of a catalyst, for example, anhydrous aluminium chloride, anhydrous zinc chloride, either alone or with phosphorus oxychloride in accordance with the reaction described by Fries, or, by a reaction of the Friedel-Craft type, whereby the chloride of an aromatic acid, unsubstituted or substituted by methoxy groups, is reacted with benzene, substituted by methoxy groups in the presence of a catalyst of the Friedel-Craft type, for example, aluminium chloride. In this case it is then necessary to release the hydroxy functions from the methoxy radicals by a known process. By such a process a compound of formula I, in which a ketone function is present may be prepared.

When it is desired to prepare a compound of formula I having a carbon-carbon double bond, an acyl chloride may be reacted with an aromatic carbide by the process described by C. Mentzer and Dat Xuong (Bul. Soc. Chem. 1947, 14, 890), to give a gem-diarylethylene, or a carbinol may be dehydrated in the presence of a dehydrating agent, for example, sulphuric acid, phosphoric acid or acetic anhydride, for example, in order to introduce a double bond into the carbon chain.

If it is desired to obtain a compound having a carbon-carbon double bond and a nitrile function, a carbonyl derivative, for example, an aldehyde or ketone is reacted with a derivative possessing an active methylene radical of the acyl-acetonitrile type, for example, as described in Org. Synth. Coll. Vol. 1967 III 715 and IV 387.

Examples of the preparation of some of the new compounds according to the present invention will be given below, but it is possible, for the preparation of known compounds, to refer to Beilstein 8, in particular for the synthesis of compounds of the benzophenone specified above, compounds such as tetrahydroxy-3,3',4,4', benzile may be synthesised by the methods of Irwin A. Pearl et al. (J. Org, Chem. 1960, 25, 1449–50) or of G. Barger et al. (J. Chem. Soc. 1907, 93 737); compounds such as tetrahydroxy-3,3',4,4', β-phenylacetophenone may be synthesised by the methods of Irwin. J. Pearl et al. cited above.

3,3',4,4'-Tetrahydroxybenzophenone may be synthesised by the process described in ("Fortschritte der Teerfarben Fabrikation" 1891, 3, 372).

The following Examples illustrate the invention:

EXAMPLE 1

Preparation of 2,3,3',4,4',5'-hexahydroxybenzophenone.

A reaction of the Fries type was used:

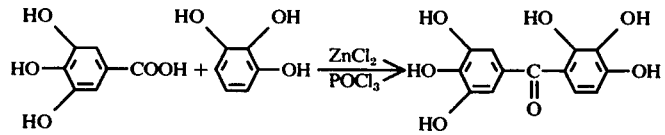

32 g of Gallic acid, 32 g of pyrogallol, 55 g of anhydrous zinc chloride and 100 cm³ of phosphorus oxychloride were mixed in a balloon flask equipped with a condenser and an ampoule of calcium chloride, and were heated to 80° C for 2 hours. After cooling the reaction mixture, a mixture of water and ice was added, whereupon the reaction product precipitated. The reaction product was washed once with water, treated with a solution of sodium bicarbonate, then washed again with water, and finally recrystallised from aqueous solution. Yield: 15 g of crystalline 2,3,3',4,4',5'-hexahydroxybenzophenone having a melting point of 270° C.

EXAMPLE 2

Preparation of 2,3,3',4'-tetrahydrobenzophenone.

A reaction of the Friedel-Craft type is used:

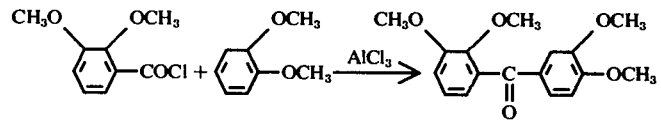

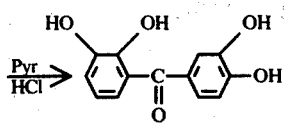

140 g of Veratrole and o-veratroyl chloride, obtained by the action of phosphorus pentachloride on 81 g of o-veratric acid, were placed in a balloon flask which was equipped with a mechanical agitator. 68 g of Anhydrous aluminium chloride were added in portions in such a manner that the temperature of the reaction mixture remained within the range of from 30° to 40° C. After 16 hours of stirring, the mixture was treated with water and ice, then extracted with chloroform. The chloroform solution was washed with water treated with a solution of sodium bicarbonate, washed again with water, dried and evaporated. The residue, which was recrystallised from methanol was 2,3,3',4'-tetramethoxybenzophenone having a melting point of 127° C.

The compound thus obtained was heated under reflux in the presence of pyridine chlorhydrate, then added to water. After recrystallisation of the resulting precipitate, crystals of 2,3,3',4'-tetrahydroxybenzophenone having a melting point of 200° C were obtained.

Elementary analysis for $C_{13}H_{10}O_5$:
Calculated (%): C 63.41 H 4.06
Found (%): C 63.14 H 4.04

EXAMPLE 3

Preparation of β-(3,4-dihydroxyphenyl)-2,3,4-trihydroxyacetophenone.

The following reaction was used:

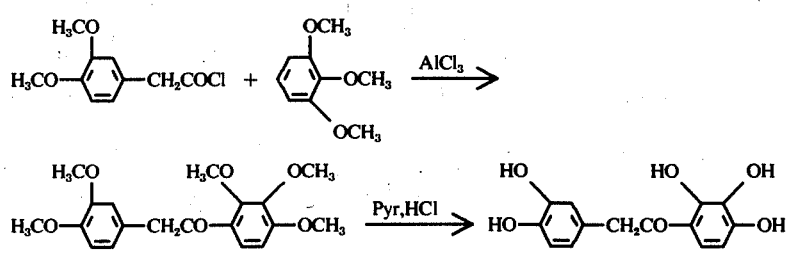

168 g of 1,2,3-Trimethoxybenzene and the chloride of homoveratric acid, which had been obtained by reacting thionyl chloride and 98 g of homoveratric acid, were mixed in a balloon flask equipped with a mechanical stirrer. 68 g of anhydrous aluminium chloride were gradually added to the mixture in such a manner that the temperature of the reaction mixture remained within the range of from 30° to 40° C. The reaction mixture was stirred for 16 hours, then treated with a mixture of water and ice, and subsequently extracted with chloroform. On recrystallisation from ethanol, 2,3,3',4,4'-pentamethoxy-desoxybenzoin having a melting point of 138° C was obtained.

The compound was heated under reflux in the presence of pyridine chlorhydrate and then the reaction mixture was added to water. The resulting precipitate consisted of β-(3,4-dihydroxyphenyl)-2,3,4-trihydroxyacetophenone and was recrytallised from water; its melting point is 155°-156° C.

Elementary analysis for $C_{14}H_{17}O_6$:
Calculated (%): C 60.86 H 4.34
Found (%): C 60.58 H 4.43.

EXAMPLE 4

Preparation of 1-phenyl-2,2-di-(2,3-dimethoxyphenyl) ethylene.

The following reaction was used:

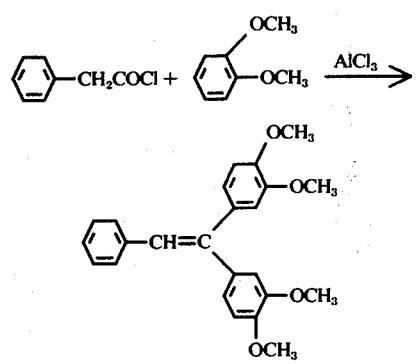

175 g of Veratrol were mixed in a balloon flask equipped with a mechanical stirrer with phenylacetic acid chloride obtained by reacting thionyl chloride with 69 g of phenylacetic acid. 68 g of Anhydrous aluminium chloride were added in portions in such a manner that the temperature of the reaction mixture remained within the range of from 30° to 40° C. When the reaction had finished, the reaction mixture was treated with ice-water and chloroform. The chloroform phase was washed with water, treated with a solution of sodium bicarbonate, washed again with water, dried and evaporated.

The resulting 1-phenyl-2,2-di-(2,3-dimethoxyphenyl) ethylene obtained was distilled at 244°–246° C under a pressure of 0.9 mm Hg. After recrystallisation from ethanol, crystals having a melting point of 138° C were obtained.

EXAMPLE 5

Preparation of 1-phenyl-2,2-di-(2,3-diacetoxyphenyl) ethylene.

The product obtained in Example 4 was heated in the presence of pyridine chlorohydrate and acetyl chloride. After recrystallisation from ethanol, crystals of 1-phenyl-2,2-di-(2,3-diacetoxyphenyl) ethylene having a melting point of 163° C were obtained.
Elementary Analysis:
Calculated (%): C 68.85 H 4.91
Found (%): C 69.62 H 4.90.

EXAMPLE 6

Preparation of 1-phenyl-2,2-di-(2,3-dibenzoyloxyphenyl) ethylene.

The product of Example 4 was heated in the presence of pyridine chlorhydrate and benzoyl chloride. On recrystallisation of the resulting compound from propanol, crystals of 1-phenyl-2,2-di-(2,3-dibenzoyloxyphenyl)-ethylene having a melting point of 90°–100° C, were obtained.
Elementary analysis for $C_{48}H_{22}O_8$
Calculated (%): C 78.30 H 4.36
Found (%): C 78.00 H 4.65

EXAMPLE 7

Preparation of di-(3,4-dimethoxyphenyl)-cyclohexylidene methane 151 g of 3,3',4,4'-Tetramethoxybenzophenone were reacted in tetrahydrofuran with the bromide of cyclohexyl magnesium, which had been prepared from 163 g of bromocyclohexane and 24.3 g of magnesium. After the reaction mixture had been hydrolysed by a solution of ammonium chloride, extracted with benzene and water, and the benzene extract dried with benzene, the compound of the following formula

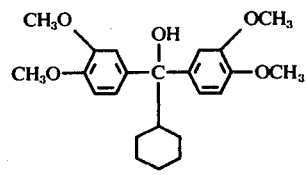

was obtained on evaporating the solution to dryness.

This alcohol was then dehydrated by excess acetyl chloride. After evaporation of the volatile components, the residue was distilled. A fraction distillation at 210°–220° C under a pressure of 0.15 mm of mercury was obtained. This fraction was recrystallised from ethanol to yield crystals of di-(3,4-dimethoxyphenyl)-cyclohexylidene methane of the formula:

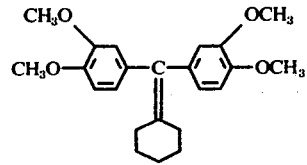

having a melting point of 107° C.

EXAMPLE 8

Preparation of di-(3,4-dibenzoyloxyphenyl) cyclohexylidene methane.

On heating the product of Example 7 in the presence of benzoyl chloride, and then treating the resulting compound with water and chloroform, a residue was obtained which on recrystallisation from propyl alcohol yielded crystals of di(dibenzoyloxy-3,4 phenyl)cyclohexylidene methane with a melting point of 176° C.
Elementary analysis for $C_{47}H_{38}O_8$
Calculated (%): C 77.47 H 4.94;
Found (%): C 77.39 H 5.11

EXAMPLE 9

Preparation of 1-phenyl-2,2-di(2',3',4'-trimethoxyphenyl) ethylene 200 g of 1,2,3-Trimethoxybenzene and phenylacetic acid chloride, obtained by the action of thionyl chloride on 68 g of phenylacetic acid, were mixed in a balloon flask equipped with a mechanical stirrer. 68 g of Anhydrous aluminium chloride were added in portions in such a manner that the temperature of the reaction mixture did not exceed 40° C, and the mixture was stirred for 16 hours. The resulting sticky mass was treated with chloroform and ice-water. The chloroform phase was washed with water, extracted with a solution of sodium bicarbonate, washed again, and dried over dry sodium sulphate, filtered and evaporated. On recrystallising the resulting oily residue, crystals of 1-phenyl-2,2-di-(2,3,4-trimethoxyphenyl) ethylene having a melting point of 120° C were obtained.

EXAMPLE 10

Preparation of 1-phenyl-2,2-di-(2',3',4'-trihydroxyphenyl) ethylene

The product of Example 9 was heated under reflux with pyridine chlorhydrate for 10 minutes then the reaction mixture was added to water. On recrystallisation of the resulting precipitate from a mixture of water and alcohol, crystals of 1-phenyl-2,2-di-(2,3,4-trihydroxyphenyl) ethylene having a melting point of 142°–143° C were obtained.

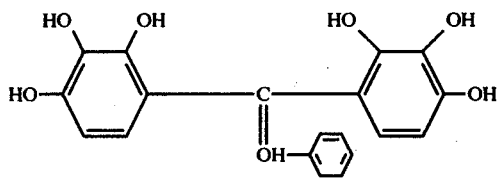

Elementary analysis for $C_{20}H_{16}O_6$
Calculated (%): C 68.2 H 4.55
Found (%): C 68.4 H 5.07

EXAMPLE 11

Preparation of 1-(3,4-dihydroxyphenyl)-2,2-diphenyl acrylonitrile 1-(3,4-dihydroxyphenyl)-2,2-diphenyl acrylonitrile was prepared by reacting benzophenone and homoveratronitrile in the presence of sodium starch as described in Org.Synth.Coll. Vol. 1963, IV, 387. On recrystallisation from acetic acid a product having a melting point of 184° C was obtained. This product was demethylated by heating in pyridine chlorhydrate. After treatment with water and recrystallisation of the precipitate from ethanol, crystals of 1-(3,4-dihydroxyphenyl)-2,2-diphenyl acrylonitrile having a melting point of 220° C were obtained.
Elementary analysis of $C_{21}H_{15}NO_2$
Calculated (%): C 80.51 H 4.79
Found (%): C 80.33 H 4.73

EXAMPLE 12

Preparation of 1,2-di-(3,4-dihydroxy) acrylonitrile

By the action of veratraldehyde on homoveratronitrile in the presence of sodium ethylate, 1,2-di-(3,4-dimethoxyphenyl) acrylonitrile was prepared according to the process described in Org.Synth.Coll. Vol. 1955 III, 715. This product, recrystallised from benzene had a melting point of 155° C.

By demethylation in the presence of pyridine chlorhydrate 1,2-di-(3,4-dihydroxyphenyl) acrylonitrile having a melting point of 240° C was obtained.

Elementary analysis of $C_{15}H_{11}NO_4$
Calculated (%): C 66.91 H 4.08
Found (%): C 66.81 H 4.32

Study of the pharmacological properties and the therapeutic applications

1. Acute toxicity on intra-peritoneal administration.

The following results were obtained from tests of acute toxicity on intraperitoneal administration of various compounds to rats:

| Compounds | DL50 A. IP | |
|---|---|---|
| 2,3,3',4,4',5'-Hexahydroxybenzophenone | 0.355 | g/kg |
| 2,3,3',4'-Tetrahydroxybenzophenone | 1.5 | g/kg |
| β-(3,4-Dihydroxyphenyl)-2,3,4-trihydroxyacetophenone | 0.73 | g/kg |

2. Acute toxicity on oral administration.

The following results were obtained from tests of acute toxicity of various compounds on oral administration to rats:

| Compounds | DL 50 A.O | |
|---|---|---|
| 2,3,3',4,4',5'-Hexahydroxybenzophenone | 1.425 | g/kg |
| 2,3,3',4'-Tetrahydroxybenzophenone | 2.0 | g/kg |
| β-(3,4-Dihydroxyphenyl)-2,3,4-trihydroxyacetophenone | 2.0 | g/kg |

3. Research into the methemoglobinising properties.

Certain phenols, in particular pyrocatechol (1,2-dihydroxybenzene) and pyrogallol (1,2,3-trihydroxybenzene), when administered either orally or parenterally to an organism bring about a transformation of the oxyhaemoglobin of the blood to methemoglobin. In oxyhaemoglobin, the iron is in the ferrous state ($Fe^{++}$) and can transport oxygen; whereas in methemoglobin, the iron is in the ferric state ($Fe^{+++}$) and is unsuitable for transporting oxygen.

The conversion of oxyhaemoglobin to methemoglobin therefore blocks the transport of oxygen in the blood and causes asphyxiation of the tissues.

It therefore appeared necessary to try to discover if the polyhydroxy compounds used in the preparations of the present invention, in particular 2,3,3',4,4',5'-hexahydroxy benzophenone, would also act as methemoglobinising agents.

This study was carried out using pyrogallol as the comparative substance and the spectrophotometric technique of Evelyn and Malby, (in R. Lecoq, 1972, Analyses Medicales, 2, p.1699):

When rats were treated for 75 days at the rate of 0.20 g per kg body weight per day, no methemoglobin could be detected in the blood of these animals.

4. Research into the oestrogenic properties.

None of the compounds used in the preparations of the invention is oestrogenic; oral or parenteral administration thereof does not cause oestrus in young rats in puberty which have recently been biovariectomised.

All the compounds of the present invention, and in particular the compounds of formula Ia, exhibit a protective effect on the catecholamines, which effect may advantageously be used in the treatment of capillary circulatory system disorders, (arteries, veins) as well as those originating from haemastasis and/or an accumulation of platelets, in particular varicose complaints and haemorroidal troubles. Certain compounds have invaluable anti-inflammation properties, and improve capilliary resistance.

5. Protection of the catecholamines.

The compounds studied have, in general, at least two hydroxyl groups situated in the ortho position relative to each other.

Whether administered orally or parenterally they undergo in the organism a monomethylation on one of the two hydroxyl groups, as do all orthodiphenols, (J. Axelrod and M. J. Laroche, 1959, Science, 130, p 800). This monomethylation is due to the action of the catechol-O-methyltransferases (C.O.M.T.), S-adenosyl-L-methionine providing the methyl radicals (J. Axelrod and R. Tomchick, 1958, J. Biol. Chem. 233 p.702). This methylation occurs in the physiological catecholamines, for example, adrenalin, as well as in the synthetic orthodiphenols.

Using the techniques of Axelrod et al (op.cit.) and J. Axelrod, S. Senoh and B. Witkop, 1958, (J.Biol.Chem. 233, p.697), it was possible to demonstrate that orthodiphenols administered to an organism act as competitors of methylation with regard to the circulating catecholamines. As methylation is a first stage in the destructive pathway, this competition serves to protect the natural catecholamines from early destruction, (J. M. Gazave, P. Canu, M. Baques, and F. Martin, 1971, Biochem and Experim. Biol., X p.89).

This property is advantageously used in the treatment of disorders of the capillary circulatory system.

Using the techniques of Axelrod et al (op.cit.) it is possible to quantify this effect for various compounds, as the intensity of the effect varies, being dependent on the chemical composition and physical properties, especially the solubility of the compound.

By incubating a catechol-O-methyltransferase with stoichiometric amounts of adrenalin and an orthodiphenol according to the method of Axelrod, determining the quantity of adrenalin protected ie. non-methylated after 30 minutes the extent of the protection given by the product studied can be evaluated. A protection of 100% has thus been discovered for 3,3',4,4'-tetrahydroxybenzophenone, 3,3',4,4',5'-pentahydroxybenzophenone, 2,3,3',4,4',5'-hexahydroxybenzophenone, 3,3',4,4'-tetrahydroxybenzile and 2,3,3',4,4'-pentahydroxybenzophenone, a protection of 90% and more for 3,3',4,4'-tetrahydroxy-β-phenylacetophenone; 2,3,3',4'-tetrahydroxybenzophenone and di-(3,4-dihydroxyphenyl) methane and a protection of less than 60% for the others.

6. Increasing capillary resistance

Experiments on capillary resistance on the guinea pig using the technique of J-L. Parrot and P. Canu, 1964, Arch. Inter, Pharmacol., 152 p.234 have shown that 2,3,3',4,4',5'-hexahydroxybenzophenone causes an increase in the capillary resistance of 82%, 2,3,3',4'- tetrahydroxybenzophenone of 56%, and β-(3,4-dihydroxyphenyl)-2,3,4-trihydroxyacetophenone of 34%. (By comparison trioxyethylrutine gives an increase of 13%).

Some of the compounds of the formula I have other interesting properties. Thus the anti-inflammation effect on vessels evaluated according to the technique of Y. Bounameaux and J. Lecomto, 1955, C.R. Soc. Biol., 149, p.624 using croton oil on mice, has illustrated the anti-inflammatory properties of 2,3,3',4'-tetrahydroxybenzophenone, 3,3',4,4',5'-pentahydroxybenzophenone, and to a lesser extent, 2,3,3',4,4',5'-hexahydroxybenzophenone.

What is claimed is:

1. A method of treating a patient suffering from a disorder caused by an increase of capillary permeability which comprises administering to such patient one to 30 mg/kg of body weight daily of a compound of the following formula:

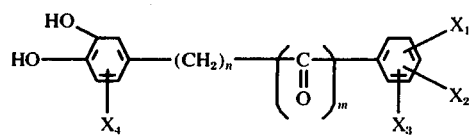

wherein $X_1$, $X_2$, $X_3$, and $X_4$ are selected from the group consisting of H and OH, $n$ is a number from 0 to 1 and $(n+m)$ equals 1 or 2, together with a pharmaceutically acceptable carrier.

2. A method of treating a patient suffering from a disorder caused by an increase of capillary permeability which comprises administrating to such a patient 1 to 30 mg/kg daily of a compound selected from the group consisting of 3,3',4,4'-tetrahydroxybenzophenone
3,3',4,4',5'-pentahydroxybenzophenone
2,3,3',4,4',5'-hexahydroxybenzophenone
3,3',4,4'-tetrahydroxybenzile
2,3,3',4,4'-pentahydroxybenzophenone
3,3',4,4'-β-phenylacetophenone
2,3,3',4'-tetrahydroxybenzophenone and
di-(3,4-dihydroxyphenyl) methane.

* * * * *